United States Patent
Shibata et al.

(10) Patent No.: US 6,850,320 B2
(45) Date of Patent: Feb. 1, 2005

(54) METHOD FOR INSPECTING DEFECTS AND AN APPARATUS FOR THE SAME

(75) Inventors: Yukihiro Shibata, Fujisawa (JP); Shunji Maeda, Yokohama (JP); Yukio Kembo, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 14 days.

(21) Appl. No.: 09/906,678

(22) Filed: Jul. 18, 2001

(65) Prior Publication Data
US 2002/0027653 A1 Mar. 7, 2002

(30) Foreign Application Priority Data

Jul. 18, 2000 (JP) .......................... 2000-222395
Apr. 2, 2001 (JP) .......................... 2001-103290

(51) Int. Cl.[7] .................. G01N 21/00; G06K 9/00
(52) U.S. Cl. .................. 356/237.3; 356/237.4; 382/149
(58) Field of Search ............... 356/237.1–237.5, 356/241.1–241.6, 238.1–238.3, 240.1; 250/559.4–559.45; 382/141, 145, 148, 149

(56) References Cited

U.S. PATENT DOCUMENTS

| | | | | |
|---|---|---|---|---|
| 4,386,850 A | * | 6/1983 | Leahy | 356/243.4 |
| 4,589,140 A | * | 5/1986 | Bishop et al. | 382/148 |
| 4,764,969 A | * | 8/1988 | Ohtombe et al. | 382/148 |
| 5,046,113 A | * | 9/1991 | Hoki | 382/147 |
| 5,153,444 A | * | 10/1992 | Maeda et al. | 250/559.05 |
| 5,173,719 A | * | 12/1992 | Taniguchi et al. | 356/394 |
| 5,649,022 A | * | 7/1997 | Maeda et al. | 382/141 |
| 5,898,491 A | * | 4/1999 | Ishiguro et al. | 356/243.4 |
| 6,072,899 A | * | 6/2000 | Irie et al. | 382/149 |
| 6,078,386 A | * | 6/2000 | Tsai et al. | 356/237.1 |
| 6,104,481 A | * | 8/2000 | Sekine et al. | 356/237.5 |
| 6,178,257 B1 | * | 1/2001 | Alumot et al. | 382/145 |
| 6,222,936 B1 | * | 4/2001 | Phan et al. | 382/149 |
| 6,292,259 B1 | * | 9/2001 | Fossey et al. | 356/237.2 |
| 6,330,354 B1 | * | 12/2001 | Companion et al. | 382/150 |
| 6,360,005 B1 | * | 3/2002 | Aloni et al. | 382/148 |
| 6,407,373 B1 | * | 6/2002 | Dotan | 250/201.3 |
| 6,411,378 B1 | * | 6/2002 | Pike | 356/237.5 |
| 6,437,862 B1 | * | 8/2002 | Miyazaki et al. | 356/237.2 |
| 6,507,933 B1 | * | 1/2003 | Kirsch et al. | 716/4 |

* cited by examiner

*Primary Examiner*—Zandra V. Smith
*Assistant Examiner*—Gordon J. Stock, Jr.
(74) *Attorney, Agent, or Firm*—Antonelli, Terry, Stout & Kraus, LLP

(57) ABSTRACT

The present invention provides a highly sensitive inspection technology that prevents false detections. The present invention includes means for detecting an image of an entire chip. Using this image, inspection regions are defined based on criticality. Detection sensitivities can be set for each of these inspection sensitivities. Alternatively, false detections can be eliminated in post-inspection processing by recording characteristic values used to evaluate defects, e.g., concentration differences, in the inspection results. Furthermore, by providing a system that allows sharing of inspection conditions and the like needed by multiple inspection devices, the time required for determining inspection conditions can be shortened and stability and reliability can be monitored.

12 Claims, 13 Drawing Sheets

FIG.7

| Defect No. | Chip X coordinate | Chip Y coordinate | In-chip X coordinate | In-chip Y coordinate | Density difference | Region | Defect X dimension | Defect Y dimension |
|---|---|---|---|---|---|---|---|---|
| 1 | 2 | 11 | 900 | 1000 | 40 | 4 | 0.2 | 0.2 |
| 2 | 3 | 1 | 1100 | 200 | 35 | 5 | 0.1 | 0.2 |
| 3 | 3 | 4 | 950 | 3000 | 32 | 4 | 0.2 | 0.1 |
| 4 | 3 | 7 | 2000 | 2400 | 42 | 5 | 0.3 | 0.2 |
| 5 | 5 | 5 | 2200 | 3200 | 38 | 6 | 0.1 | 0.2 |
| 6 | 7 | 6 | 2800 | 3300 | 32 | 4 | 0.1 | 0.1 |
| 7 | 7 | 23 | 3000 | 200 | 31 | 6 | 0.1 | 0.2 |
| 8 | 7 | 8 | 3400 | 3500 | 38 | 5 | 0.1 | 0.2 |
| 9 | 7 | 6 | 5000 | 1900 | 37 | 6 | 0.2 | 0.2 |
| 10 | 8 | 11 | 5200 | 1700 | 50 | 6 | 0.4 | 0.2 |

FIG.8

| | Features | Description |
|---|---|---|
| 1 | Extract review defects by criticality region | Changes reviewing rate based on criticality of detected defects |
| 2 | Extract review defects according to false detection rate | If detected defect coordinates are in a region with a high false detection rate, the concentration difference threshold value is increased, the defect is re-evaluated, and the detected defect is reviewed |
| 3 | Superimpose defects by wafer product type | Defects detected on the entire wafer surface are displayed on a chip image to allow review defect selection |
| 4 | Share recipe data among different inspection device types | Sharing of theta alignment target coordinates, chip arrangement information, in-chip inspection region coordinates, and chip images |
| 5 | Evaluate sensitivity of different inspection devices | One wafer is inspected by multiple inspection devices, defect coordinates are compared, sensitivities of inspection devices are compared, and detected defect modes are analyzed |
| 6 | Stability management for inspection devices | A specific wafer is inspected periodically, and inspection sensitivity is monitored |
| 7 | Stability management for production devices | Defect counts by category from review results are statistically processed and defect generation candidate devices are extracted |

FIG.12

(a) Inspection results 1

| No | Die X coord-inate | Die Y coord-inate | In-die X coord-inate | In-die Y coord-inate |
|---|---|---|---|---|
| 1 | 1 | 1 | 102 μm | 1540 μm |
| 2 | 1 | 1 | 1050 | 2050 |
| 3 | 1 | 2 | 750 | 1050 |
| 4 | 1 | 2 | 3000 | 220 |
| 5 | 1 | 3 | 550 | 3500 |
| 6 | 1 | 4 | 2350 | 1850 |
| | | ⋮ | | |

(b) Inspection results 2

| No | Die X coord-inate | Die Y coord-inate | In-die X coord-inate | In-die Y coord-inate |
|---|---|---|---|---|
| 1 | 1 | 1 | 105 μm | 1543 μm |
| 2 | 1 | 2 | 753 | 1050 |
| 3 | 1 | 2 | 1555 | 350 |
| 4 | 1 | 2 | 2500 | 3050 |
| 5 | 1 | 4 | 850 | 1350 |
| 6 | 1 | 4 | 2350 | 1850 |
| | | ⋮ | | |

(c) Composite inspection results

| No | Die X coord-inate | Die Y coord-inate | In-die X coord-inate | In-die Y coord-inate | Inspe-ction 1 | Inspe-ction 2 |
|---|---|---|---|---|---|---|
| 1 | 1 | 1 | 102 | 1540 | 1 | 1 |
| 2 | 1 | 1 | 1050 | 2050 | 1 | 0 |
| 3 | 1 | 2 | 750 | 1050 | 1 | 1 |
| 4 | 1 | 2 | 1555 | 350 | 0 | 1 |
| 5 | 1 | 2 | 2500 | 3050 | 0 | 1 |
| 6 | 1 | 2 | 3000 | 220 | 1 | 0 |
| 7 | 1 | 3 | 550 | 3500 | 0 | 1 |
| 8 | 1 | 4 | 850 | 1350 | 1 | 0 |
| 9 | 1 | 4 | 2350 | 1850 | 1 | 1 |
| | | | ⋮ | | | |

METHOD FOR INSPECTING DEFECTS AND AN APPARATUS FOR THE SAME

BACKGROUND OF THE INVENTION

The present invention relates to a method for inspecting defects and a device for the same to be used in inspecting and observing fine pattern defects, particles, and the like in production processes, e.g., semiconductor production processes and flat panel display production processes.

An example of a conventional inspection technology relating to the present invention can be found in an inspection device described in pgs. 12–15 of "Clean Technology" (September 1998, Nikkan Kougyou Shuppan, Ltd.).

In this description, non-critical false detentions caused by color discrepancies are prevented from being detected using a floating threshold value algorithm referred to as a segmented auto-threshold algorithm.

This type of conventional technology provides an algorithm for providing threshold values by determining, for individual segments, contrasts and image brightnesses of patterns formed on a specimen. In this algorithm, if pattern contrast or image brightness is high, the threshold value is increased so that inspection sensitivity is decreased. Improving yield in semiconductor production processes requires detecting killer defects at an early stage. With the conventional technology, killer defects may be missed depending on the detected image. Furthermore, with the floating threshold values of the conventional technology, not all false detections may be eliminated depending on color discrepancy conditions.

Also, the conventional technology described above presents three types of inspection devices, and inspection conditions must be created for each of these devices. Generating inspection conditions for each of these devices is time-consuming.

Furthermore, inspection devices need to provide stable sensitivity, but detection sensitivity can vary due to factors such as variations in the light-emission point of the light source of an optical system. As a result, phenomena such as decreased inspection sensitivity over time is possible. Since decreased inspection sensitivity can lead to missed killer defects, monitoring the inspection sensitivity of the device and detecting irregularities quickly can contribute to improved product yield.

SUMMARY OF THE INVENTION

The present invention provides a defect detection technology that is highly sensitive and that limits false detections. Also, the present invention provides a defect inspection/detection technology that can reduce the time required to generate conditions for inspection devices.

According to the present invention, an inspection method and device is provided wherein an optical system retrieves images of individual chips formed on a specimen to be inspected. The chip image is displayed and multiple regions are defined according to criticality. Adjustable threshold values are used to evaluate defects by these defined regions.

According to another aspect of the present invention, an inspection information management system stores results of evaluations determining whether defect candidates detected by an inspection device are defects or false detections. Regions containing a high number of false detections are statistically processed so that defect candidates detected in regions with many false detections are excluded from being reviewed, thus reducing the probability that defect candidates detected in regions with many false detections will be reviewed.

According to another aspect of the present invention, a high-level inspection information management system is equipped with a communication system and format sharing software. The communication system allows information such as inspection conditions shared by multiple inspection devices to be passed back and forth among these inspection devices. The format sharing software allows the inspection condition formats of the inspection devices to be shared. Thus, inspection conditions created by one of the devices can be used by other inspection devices, thus improving the efficiency of determining inspection conditions.

According to another aspect of the present invention, an inspection information management system stores results of evaluations determining whether defect candidates detected by an inspection device are defects or false detections. Regions containing a high number of false detections are statistically processed so that defect candidates detected in regions with many false detections are [?excluded from being?] reviewed, thus reducing the probability that defect candidates detected in regions with many false detections will be reviewed.

According to another aspect of the present invention, an inspection information management system periodically inspects specific specimens and saves the results. By comparing inspection results with prior inspection results, the variations in inspection sensitivity can be calculated, thus allowing the stability of the inspection device to be monitored.

Furthermore, according to another aspect of the present invention, an inspection information management system stores statistical data on defect generating devices and defect categories beforehand. Defect generating device candidates are extracted based on categorization results of defects detected by an inspection device. This reduces the time between defect detection and when measures can be taken for the defect generating device.

These and other objects, features and advantages of the invention will be apparent from the following more particular description of preferred embodiments of the invention, as illustrated in the accompanying drawings.

BRIEF DESCRIPTION OF THE DRAWINGS

FIG. 7 is a drawing showing an embodiment of an inspection results output format of an inspection device.

FIG. 8 is a drawing showing a list of features of an inspection information management system according to the present invention.

FIG. 12 shows results of combining detection results inspected according to two recipes.

DESCRIPTION OF THE PREFERRED EMBODIMENTS

The following is a description of embodiments of the present invention, with references to the figures.

Figure 1:
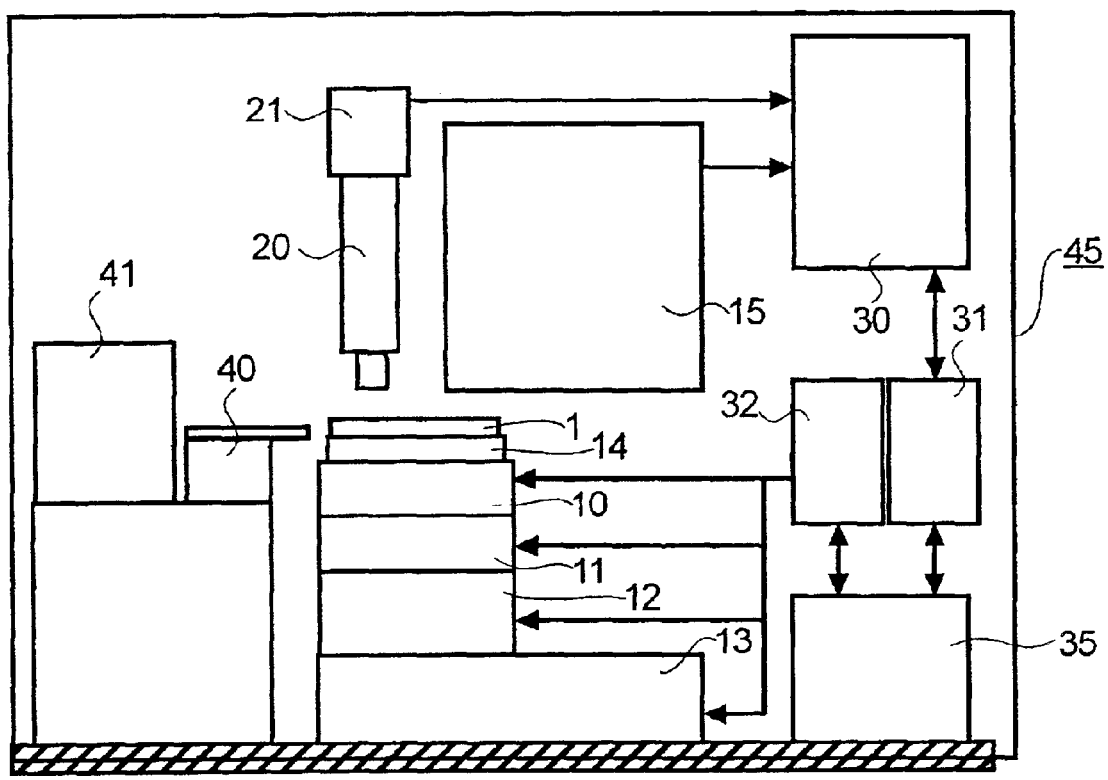
FIG. 1 is a block diagram showing a sample architecture of an optical visual inspection device according to an embodiment of the inspection device of the present invention.

FIG. 1 is a block diagram showing an optical visual inspection device 45 according to an embodiment of an inspection device according to the present invention. In the figure, a specimen (wafer) 1 is housed in a wafer cassette 41 and is mounted on a wafer mounting base 14 by a wafer transport robot 40. This wafer mounting base 14 is moved along the Z axis, the X axis, the Y axis, and is rotated by a Z stage 10, a θ stage 11, an X stage 12, and a Y stage 13.

The wafer 1 transported to the wafer mounting base 14 is moved inside the field of view of a chip detection optical system 20 to detect an image of the entire area of the chip.

Next, a camera 21 with a magnification generates a chip image. This image is transferred to an image processing module 30, and this image is saved in a data server 31. In this system, the image can be displayed on a display of an operating computer 35 of the inspection device.

In the actual inspections, the image is detected by scanning the surface of the wafer 1 within the field of view of a visual inspection optical system 15 with a magnification. This image data is transferred to the image processing module 30. Comparisons are made with an adjacent chip to determine defect candidates. The results of this are stored in the data server 31. During the review operation, the inspection results are read, The mechanical operations of the stage 10 through the stage 13 and the like are controlled by a mechanical controller 32.

The wafer 1 transported onto the wafer mounting base 14 must be adjusted to provide alignment for the multiple chips 2 formed on the wafer 1 and for flatness of the X, Y stages 12, 13. The multiple chips 2 each have identical patterns or a plurality of identical sets of patterns. To perform θ alignment, the positions of two pattern points formed on the wafer I are detected and the θ offset is corrected with the θ stage 11.

Figure 2:
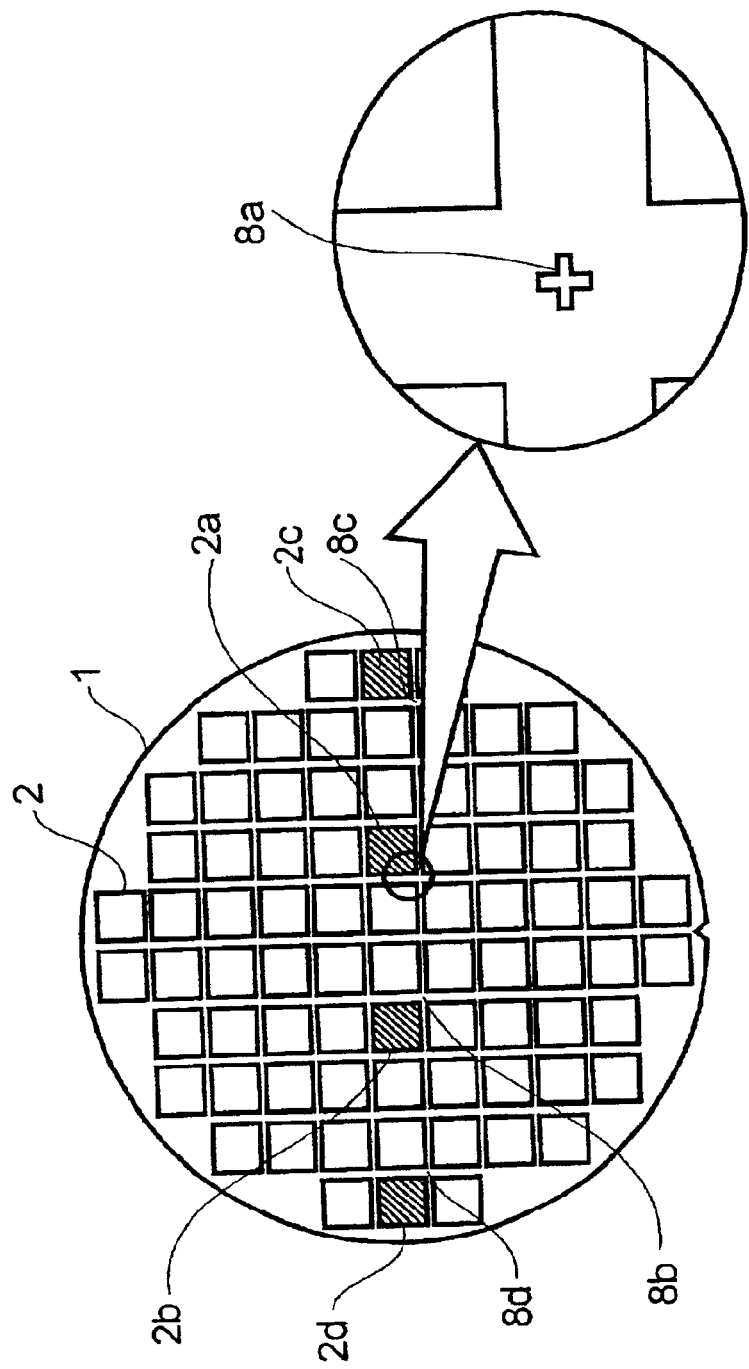
FIG. 2 is a plan drawing of a semiconductor wafer for the purpose of describing θ alignment.

The following is a description of how θ alignment is performed, with references to FIG. 2.

FIG. 2 is a plan drawing of a semiconductor wafer. To determine the θ positioning of the wafer in the figure, a first θ alignment is performed using a wide field of view and low-magnification optical conditions. Then, a second θ alignment is performed using a narrow field of view and high-magnification optical conditions. This provides high-precision θ positioning.

To do this, two chips to be used for θ alignment must be determined. Chips 2a, 2b are selected for the first θ alignment. For example, cross marks 8 in the scribe area can be registered as the θ alignment patterns for these chips 2a, 2b. The two chips 2a, 2b are inspected separately, and cross marks 8a, 8b are detected under low-magnification optical conditions to determine their X- and Y-axis coordinates.

The θ offset is calculated from the coordinates of these two points. Based on this offset, the θ stage 11 is moved to perform a first θ correction. In the second θ alignment, two chips 2c, 2d separated further apart from each other than the chips used in the first θ alignment are selected. As in the first alignment, cross marks 8c, 8d of the chips 2c, 2d are detected separately under high-magnification optical conditions, and the θ stage 11 is used to perform a second correction. Information such as the coordinates within the wafer of the chips and the cross marks used to perform θ alignment can be shared for use by different types of inspection devices other than the optical visual inspection device 45.

Allowing communication of information between the different types of inspection devices is an efficient way to share such information. To provide this, it is necessary to set up an inspection information management system that collects the various information from the inspection devices used in the semiconductor production line.

Figure 3:
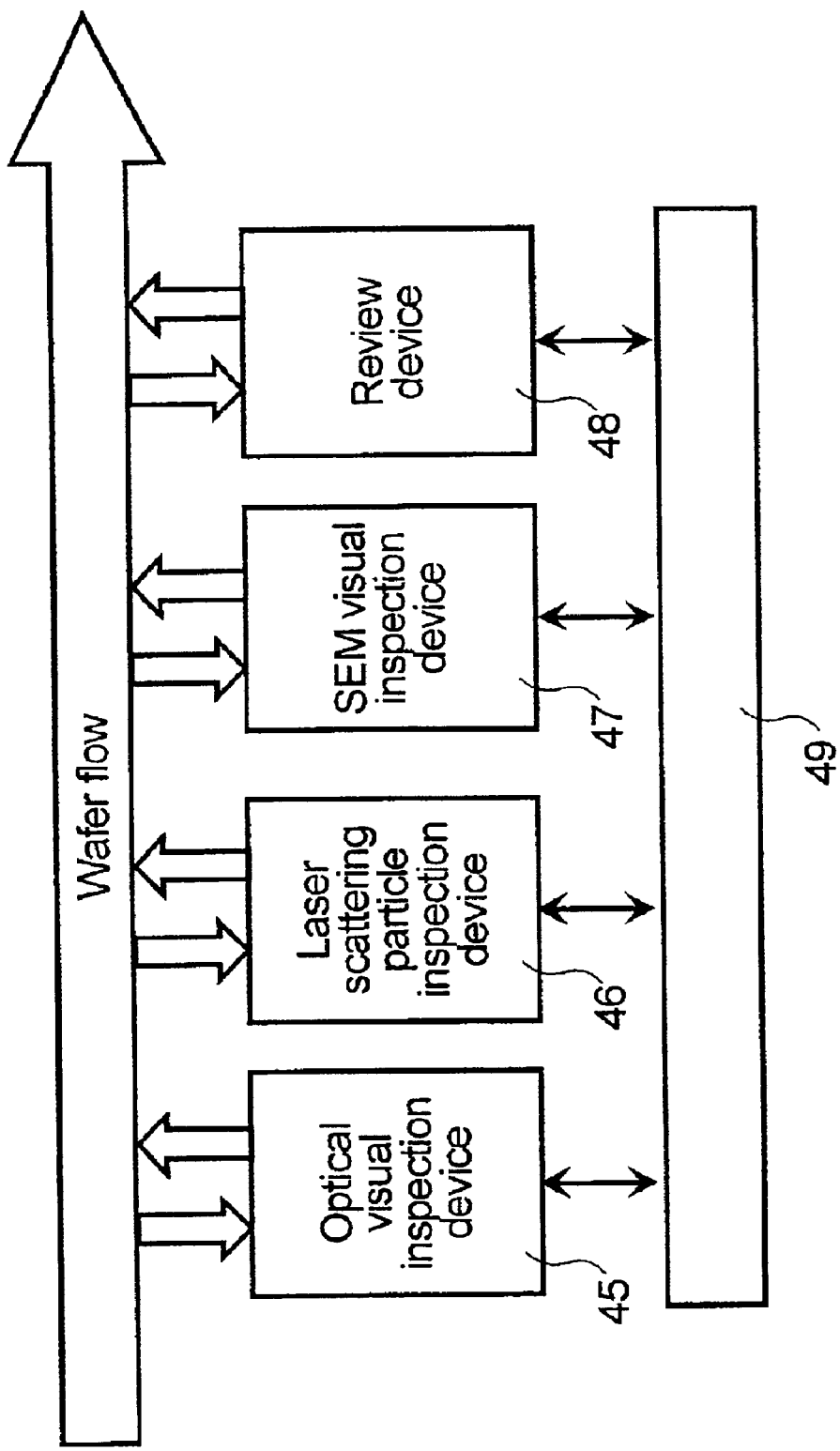
FIG. 3 is a block diagram showing an embodiment of an inspection information management system according to the present invention.

FIG. 3 is a block diagram showing an embodiment of an inspection information management system according to the present invention. For example, in a production line that involves inspecting semiconductor wafers or the like, the optical visual inspection device 45, a laser-scattering optical detection type contaminant detection device 46, an SEM (scanning electron microscope) visual inspection device 47, a review SEM 48 may be arranged along the semiconductor chip flow. In this embodiment, a shared inspection information management system 49 is provided for these devices, allowing communication between these inspection devices. As a result, this shared inspection information management system 49 allows inspection conditions and the like to be passed back and forth.

For example, if a new type of wafer 1 is sent down the production line, the optical visual inspection device 45 first registers the chips to be used for θ alignment and indicates chip arrangement information, detection regions, and the like. This data is saved in the inspection information management system 49.

As a result, the other inspection devices can use the information already prepared by the optical visual inspection device 45 to make updates, eliminating the need for generating new inspection conditions. Thus, the time required for generating inspection conditions can be reduced and the time required for the actual inspection of the wafer 1 is reduced as well. This improves the effective operating efficiency.

Figure 4:
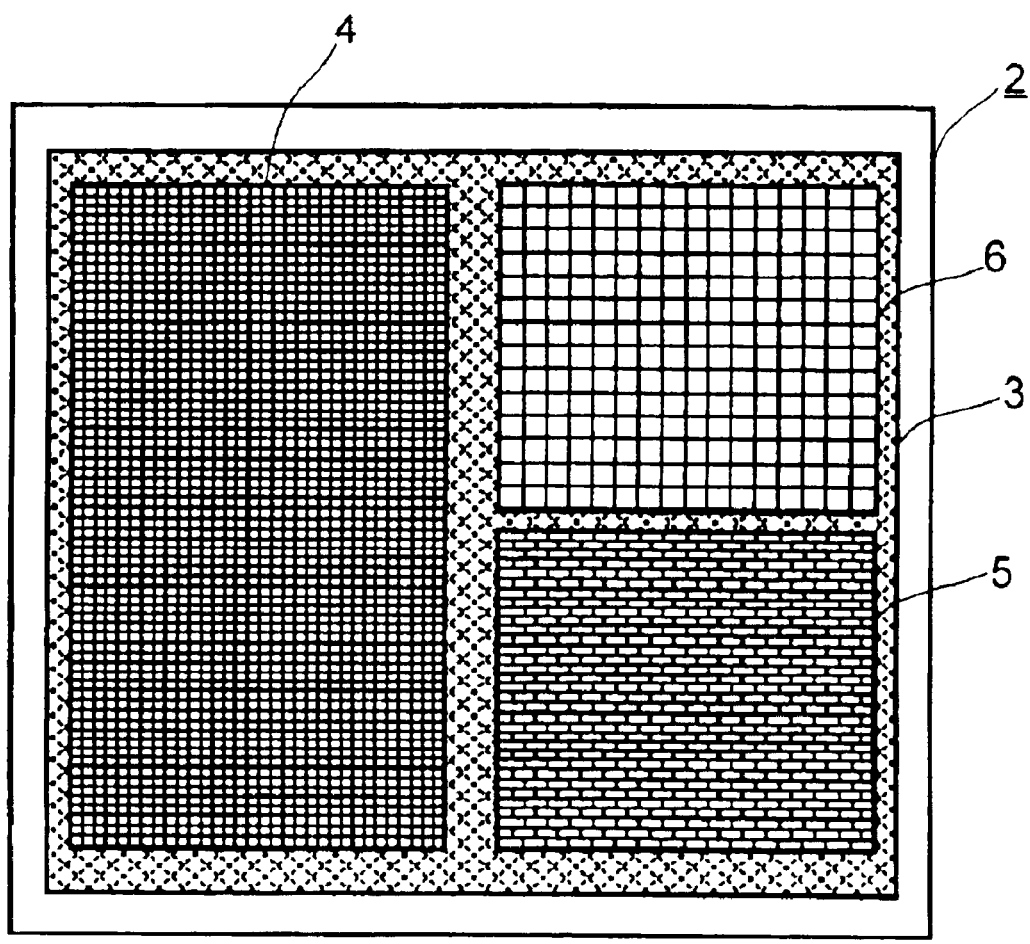
FIG. 4 is a drawing of a semiconductor chip.

The following is a description of how the image obtained by the chip detection optical system 20 shown in FIG. 1 is used, with references to FIG. 4.

FIG. 4 shows a visual drawing of a semiconductor chip. As shown in FIG. 4, an LSI the includes both memory and logic circuits can be divided according to regions in the chip, e.g., a memory section 4, a logic section 5, and a peripheral circuits section 6 containing an interface section and the like. Degrees of criticality can vary depending on factors such as the different pattern design rules that are used in each of these regions, and also the type of patterns to be layered later.

For example, the memory section 4 uses the narrowest design rule, and there is a higher probability that small particles and pattern defects can lead to killer defects. In the peripheral circuits section 6, however, the pattern design rule is relatively wide, and the space between patterns is wider as well. Thus, the size of defects that lead to killer defects is larger than that of the memory section 4.

Generally, wafers that have undergone CMP (Chemical Mechanical Polishing) tend to have significant color irregularities in spaces of the wafer that do not contain patterns.

Since the peripheral circuits section 6 has a high threshold for killer defects and tends to produce false detections due to discoloration, the rate of false detections can be lowered by using less sensitivity when inspecting the peripheral circuits section 6. Thus, efficient detection can be provided by displaying an image of the entire inspection region 3 of the chip 2 and using this display to divide up inspection regions based on killer defect thresholds.

Figure 5:
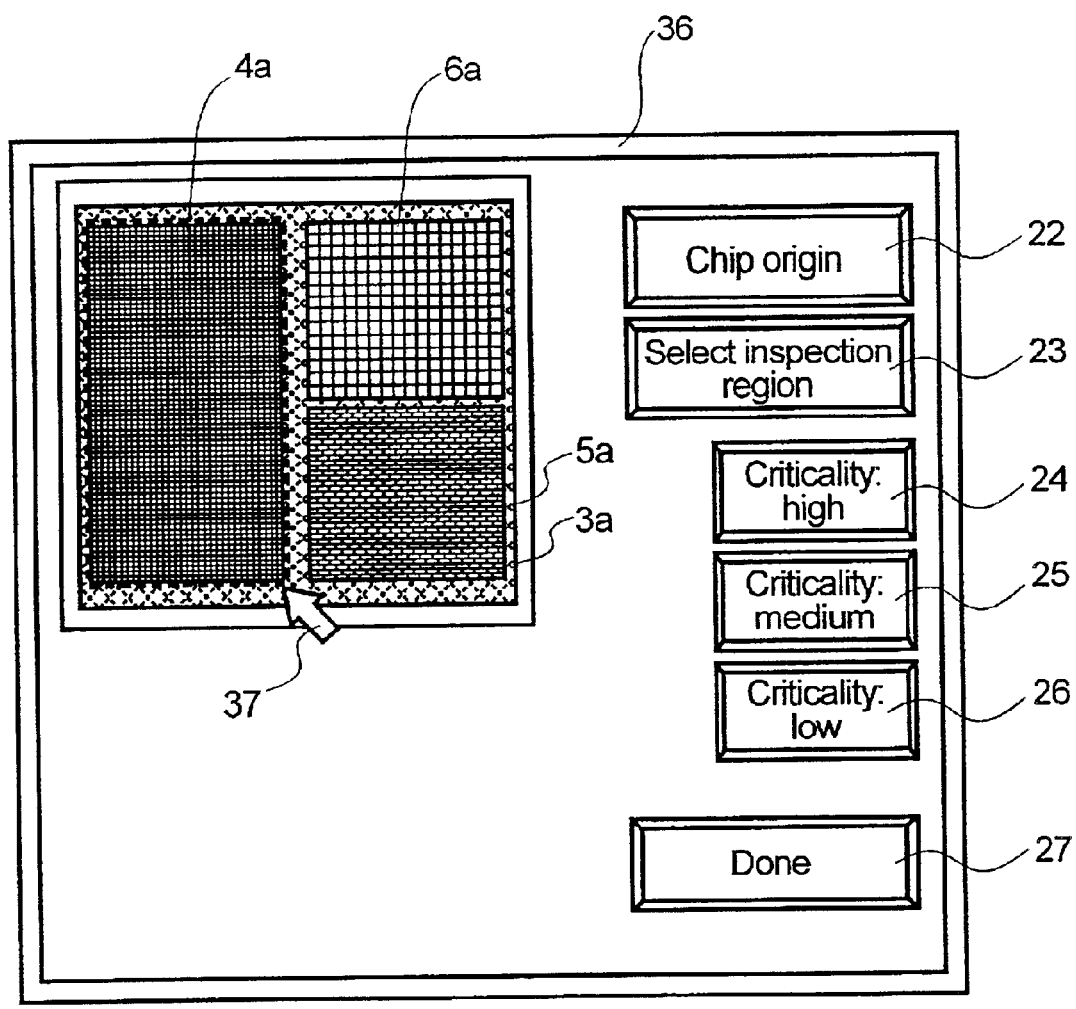
FIG. 5 is a drawing of a display allowing regions to be defined within a semiconductor chip.

Next, a method for dividing up chip inspection regions using the display from the operating computer 35 shown in FIG. 1 will be described, with references to FIG. 5. FIG. 5 shows a display that allows chip regions to be divided up. As the figure shows, a display 36 shows an image of the entire chip.

First, a position to be used as the origin point on this chip is registered using this screen. Registration is performed by clicking a "chip origin" button 22, moving a cursor 37 with a mouse, and clicking an origin point on the screen. To define an inspection region, a "select inspection region" button 23 is clicked, and a button corresponding to criticality is clicked.

For example, to register the region for a memory section 4a in the inspection area 3a, a "criticality: high" button 24 is clicked, and the image of the memory section 4a is selected with the cursor. Since a peripheral circuits section 6a has a high killer defect threshold, a "criticality; low" button 26 can be clicked, for example, when specifying the image for the peripheral circuits sections 6a.

Also, to indicate a logic section 5a, which has a killer defect size threshold that is between that of the memory section 4a and the peripheral circuits section 6a, as a detection region, a "criticality: medium" button 25 is clicked to register the criticality setting.

Regions are registered in this manner one by one based on criticality of the circuit pattern. This allows chip regions to be divided up easily. If the region boundaries need to be specified more carefully, detailed specifications can be made using methods such as monitoring images of the boundaries under high-magnification optical conditions.

Besides methods for dividing up a chip into regions that use the image of the entire chip, it would also be possible to implement a method where design data, reticle pattern information, and the like are used to obtain pattern density information and inspections are performed based on evaluations of criticality levels.

Design data includes data about design rules, patterns, pattern densities, design rules of patterns layered over in subsequent processes, and the like. Thus, this information can be used to divide regions based on criticality.

Next, a method for using the inspection results for multiple regions within a chip will be described using FIG. 6.

Figure 6:
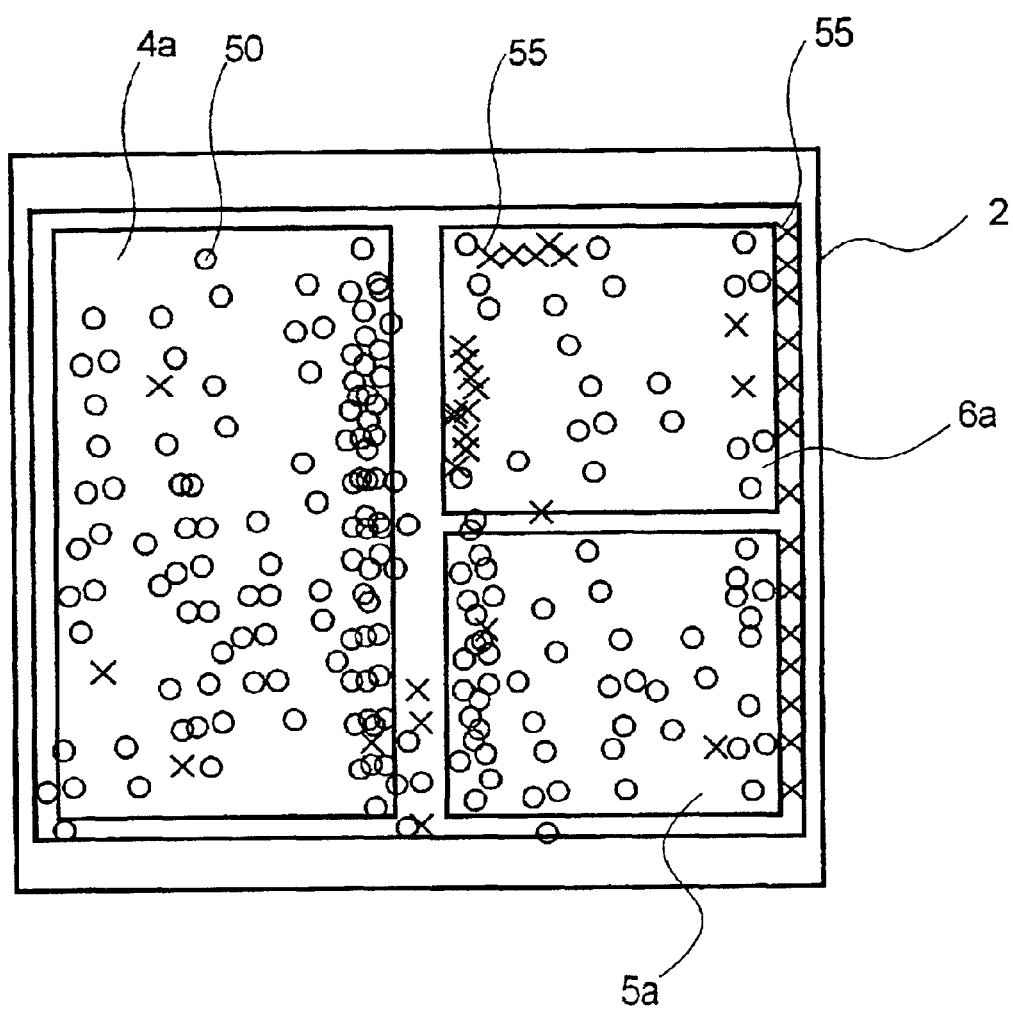
FIG. 6 is a defect display diagram in which defects detected on an entire semiconductor wafer surface are plotted on a semiconductor chip.

FIG. 6 is a defect display diagram in which defects detected on the entire wafer surface are plotted over a semiconductor chip. In the figure, white circles indicate real defects 50 and crosses indicate false detections 55. The defects detected in the inspection of the entire surface of the wafer 1 can be plotted, for example, over the full image of a semiconductor chip 2. In other words, the defects detected for all the semiconductor chips 2 in the wafer 1 are displayed on the chip coordinates for a single-chip image.

By reviewing these defects and evaluating defects and false detections, it can be determined, for example, that the peripheral circuits section 6a has a high rate of false detections. Based on this, it can be determined that the defect candidate evaluation threshold value for the peripheral circuits section 6a is low and the sensitivity setting is too high. Thus, false detections can be reduced by setting the defect candidate evaluation threshold value for the peripheral circuits section 6a to a relatively high level in a subsequent inspection. After registering criticality to each region, the "Done" button 27 is clicked to finish the registration step.

Besides varying the defect candidate evaluation threshold value for individual regions, it would also be possible to reduce false detections in post-processing operations performed on the inspection results. This will be described using FIG. 7.

The inspection results indicate defect numbers, chip X coordinates (the chip number in the horizontal direction), chip Y coordinates (the chip number in the vertical direction), in-chip X coordinates (X coordinate within the chip), and in-chip Y coordinates (Y coordinate within the chip). This allows the positions of defects on the wafer to be determined.

Also, an approximate dimensions for defects are recorded. Also, density differences of defect candidates and the regions containing the defects are recorded in the inspection results. If the density difference is large, the probability that the candidate is a false detection is low and the probability that the candidate is a defect is high. Thus, in regions with high false detection rates, these results are used to set an updated defect candidate evaluation threshold value, and defect candidates are re-evaluated.

For example, if false detections are frequent in the region 6 and the updated defect candidate evaluation threshold value is set to 35, candidates with density differences of 34 or less will not be detected. By re-evaluating defect candidates in this manner and extracting candidates with density differences of at least 35, the defect number 7, for example, will be considered to have a high probability of being a false detection since the density difference is 31 and will not be evaluated as a defect. By performing a review with false detections of this kind excluded, the probability that false detections will be reviewed will be lowered.

Also, by reducing the rate at which false detections are reviewed, the reviewing operation can be performed with the exclusion of false detections that are not killer defects. As a result, killer defects and defect-generating processes can be discovered early. This provides improved product yield.

Next, a production line equipped with an inspection management system that uses the inspection information management system 49 shown in FIG. 3 can provide the features indicated in FIG. 8.

FIG. 8 shows a list of features of an inspection management systems according to the present invention.

According to a first feature, the proportion of defects to be reviewed is varied according to criticality regions within the chip. For example, if the pattern density is high, a 90% review may be performed while 60% reviews are performed for other regions. Thus, a larger number of defects is reviewed in high criticality regions and a smaller number of defects is reviewed in low criticality regions.

In practice, the inception results from inspection devices are transferred to the inspection information management system 49 and the defects to be reviewed are extracted by the inspection information management system 49. Then, the extraction results are transferred to the reviewing device 48, and a review is performed.

Current and future reviewing operations will tend to involve implementation of automatic defect classification. In automatic defect classifications, images of defects are obtained using optical microscopes or SEMs, and these images are processed to provide automatic classification of defects. The inspection information management system 49 can be used for defect extraction in automatic defect classification as well.

According to a second feature, defects to be reviewed are extracted based on false detection rates. In this feature, statistical data for candidates evaluated to be false detections through reviews or automatic defect classification is obtained, and defects are re-evaluated with a higher defect candidate evaluation threshold value if the coordinates of the defects detected by the inspection device lie within a region having high false detection rates.

This eliminates false detections by using the fact that false detections tend to occur in specific regions or corresponding positions within the in-chip coordinates. The reliability of statistical data for false detections can be improved by accumulating all coordinates in wafers for multiple wafers inspected in the production line.

According to a third feature, defect maps from specific wafer product types and from specific processes can be superimposed.

As shown in FIG. 6, certain in-chip regions can tend to generate defects. For example, by superimposing defects detected on an entire wafer surface onto a single chip image, regions and coordinates where defects tend to occur can be easily viewed. Regions with a high number of defects are often the result of defects caused by a specific factor. In such cases, the visual appearance of the defects will be similar, so reviewing these clustered defects will only use up reviewing time. Thus, the inspection information management system 49 determines the extent of reviewing to be performed on clustered defect areas, and the resulting coordinate information is transferred to the reviewing device 48 (see FIG. 3).

Also, defect maps can be superimposed on a more macro level, i.e., the defect data from the entire surface of a wafer can be superimposed onto multiple wafers. Superimposing data from multiple wafers is useful in determining which sections of wafers tend to generate defects. Also, by using color discrepancy information for the entire wafer surface, the macro-level distribution of areas in wafers that tend to generate false detections can be determined. By using this information about areas that tend to generate false detections and information about defect distribution obtained by superimposing wafer data, the wafer surface distribution of defects not including false detections can be determined. Using this distribution information, defect generation factors can be determined with a higher reliability.

According to a fourth feature, different types of inspection devices, e.g., the optical visual inspection device 45, the laser-scattering optical detection type contaminant detection device 46, and the SEM (scanning electron microscope) visual inspection device 47, can share inspection conditions data. The θ alignment target coordinates, chip alignment information, in-chip inspection region coordinates, full chip image, and the like are transferred to the inspection information management system 49. In this system, when one of the inspection devices generates inspection conditions, information that can be shared can be transferred to other inspection devices. As a result, the time required to generate inspection conditions can be reduced.

According to a fifth feature, when different types of inspection devices are available, an evaluation must be made to determine which inspection device is to be used to inspect a mass-produced wafer. Thus, if a wafer with a new product type or process comes down the production line, a single wafer must be inspected by each of the inspection devices and inspection results sensitivities for the different devices must be compared. In other words, the inspection devices inspect the same wafer and provide inspection results. These inspection results are collected by the inspection information management system 49, which then determines the inspection device most suited for inspection of the mass-produced wafer.

In this case, the following evaluation factors can be considered.

1. Are defects with dimensions that result in killer defects detected?

2. Are defects with killer modes detected?

A "killer mode" refers to pattern defects formed on the same layer in a wafer and vertical pattern defects generated at contact holes that connect upper-layer and lower-layer patterns.

According to a sixth feature, the present invention can be used as a tool for managing stability and reliability of the different inspection devices. For example, in the optical visual inspection device 45, detection sensitivity can vary based on variations in the light emission point of the light source in the optical system. As a result, phenomena such as decreased detection sensitivity over time can take place. If detection sensitivity decreases, killer defects can be missed. By monitoring the detection sensitivity of the device, irregularities can be detected easily, thus contributing to improved product yield.

Thus, specific wafers must be inspected periodically to monitor detection sensitivity. The inspection results are transferred to the inspection information management system 49 to determine whether sensitivity is within specifications. Also, variation can be monitored so that sudden changes are clearly detected. Furthermore, if multiple identical device types are in a production line, the inspection information management system 49 can also be used as a tool to evaluate variations between the devices.

According to a seventh feature, the present invention can be used to manage stability and reliability of the production device. Defect counts are accumulated by defect type, wafer product type, and process in the inspection information management system 49. For each category, measures to reduce defects and devices generating defects are registered in the inspection information management system 49. By using this statistical data, possible defect generation factors and defect generating devices can be generated if the inspection/categorization results of wafers going down the production line exceeds a standard value. This can allow measures to be taken at an early stage.

Figure 9:
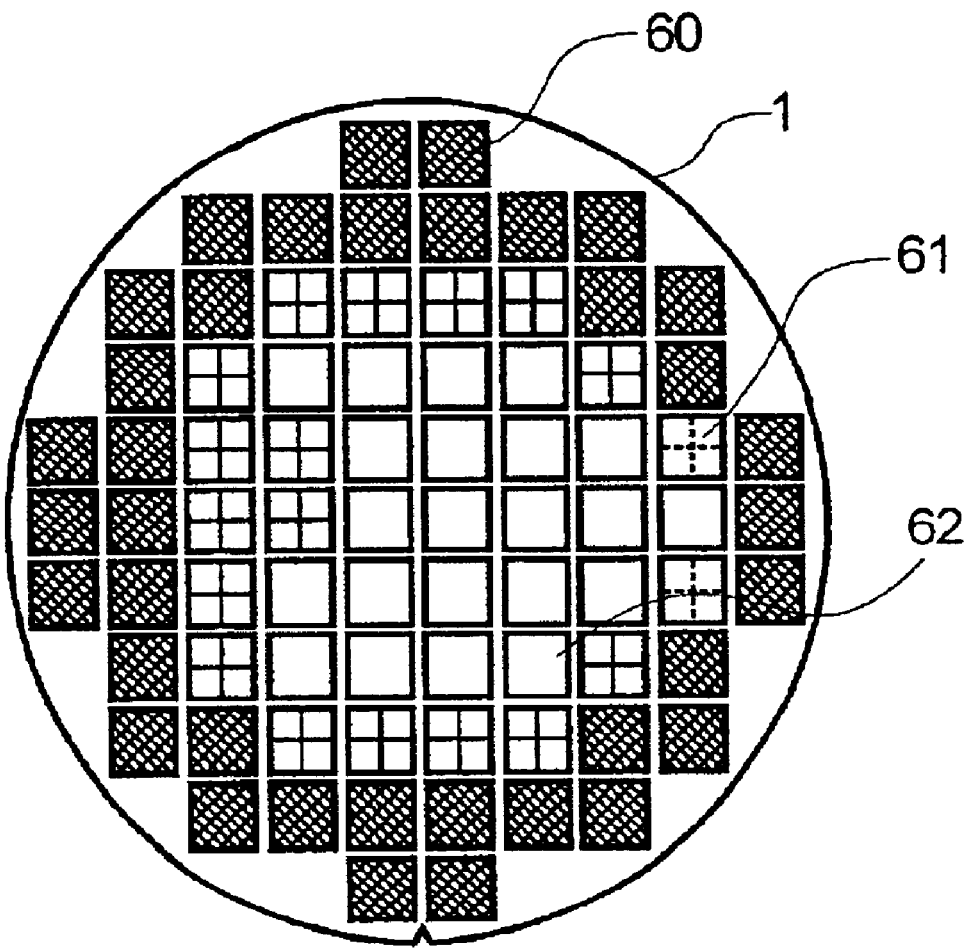
FIG. 9 is a plan drawing of a semiconductor wafer from a camera image used in macro-level inspection.

The following is a description of macro-level inspections using images of entire chips, with references to FIG. 9.

FIG. 9 shows a plan drawing of a wafer used for macro-level inspections. To perform a macro-level inspection for the wafer 1 shown in FIG. 9, chip images are obtained using step-and-repeat operations for each of chips 60 formed on the wafer 1. Differential images between images of adjacent chips are determined, and, for example, sums of the differential images are determined. For example, the sum of the differences for the chips 60 at the periphery of the wafer may be high while the sum for the chips 62 at the center of the wafer may be low, and intermediate chips 61 might have intermediate sums.

This difference results from differences in reflectance caused by factors such as variations in the thickness of the insulative film formed on adjacent chips. Thus, if the sums of the differences are large, there is a greater tendency to generate false detections. To reduce these false detections, threshold values for individual chips can be adjusted according to the sum of the differential images with adjacent chips, based on the chip images.

More specifically, chips with large sums of differences would use a higher threshold value to decrease sensitivity. It would also be possible to divide up regions within the chips that generate large sums of differences so that different threshold values can be set up for these regions.

This method is useful when chips are automatically divided up into internal regions as shown in FIG. 5. When regions are divided up automatically, the differential images of multiple chips can be integrated to provide appropriate partitioning.

Next, a procedure for setting up threshold values for individual chips based on chip images will be described, with references to FIG. 10.

Figure 10:
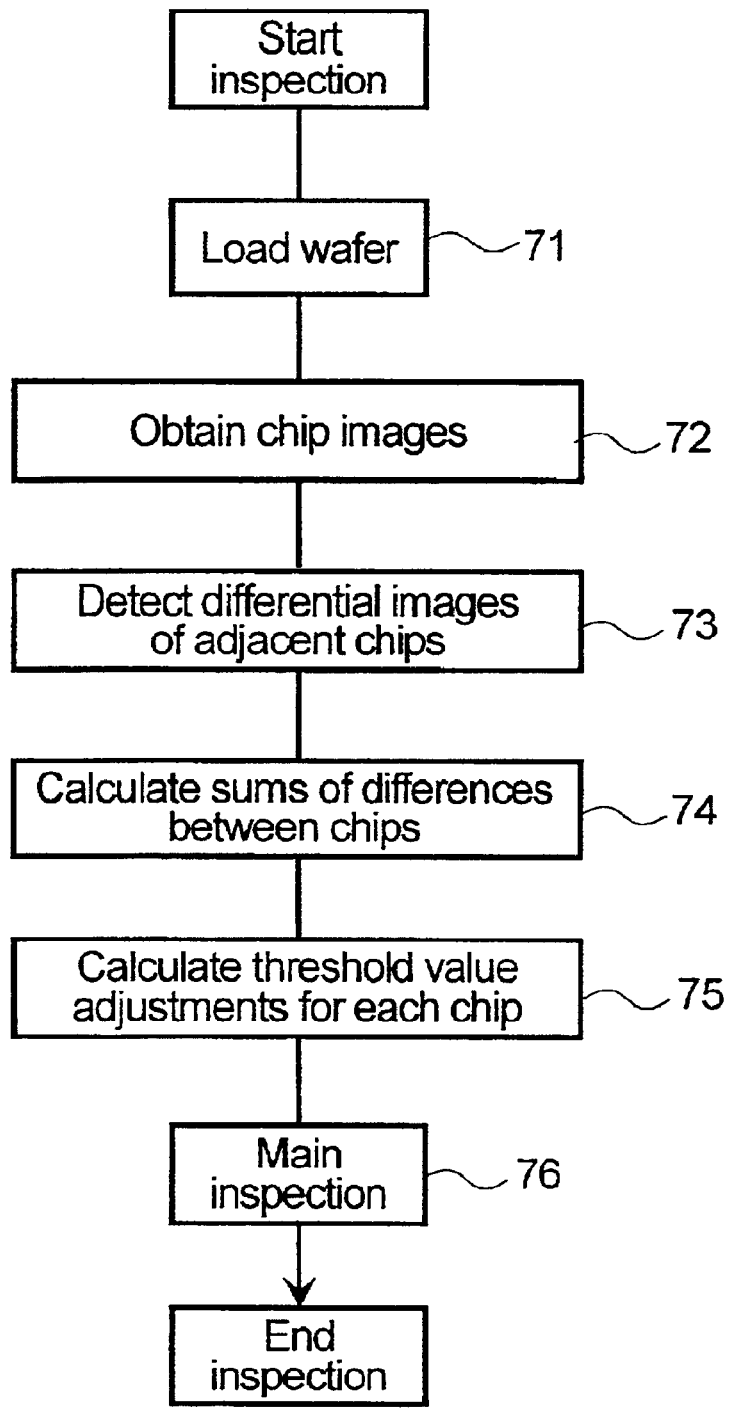
FIG. 10 is a flowchart showing a procedure for performing macro-level visual inspections using a camera image.

FIG. 10 is a flowchart showing the procedure for performing macro visual inspections using camera images. In an inspection operation, the wafer is first loaded into the inspection device at step 71. At step 72, chip images are obtained. This capturing operations is performed by stepping and repeating.

When adjacent chip images have been detected, differential images are obtained at step 73. At step 74, the totals of the differences for the chips are determined. At step 75, the value to be added to or subtracted from a threshold value for the main inspection operation is determined for each chip based on the sum of the differences. At step 76, the main inspection operation is performed and defects are extracted using the threshold values determined previously. As a result, false detections caused by macro-level color discrepancies and the like can be eliminated.

Also, the differential images based on the chip images contain information about the thicknesses of the insulative film over the chips and the like, and this information can be used in macro-level inspections of film thickness and the like.

Figure 11:
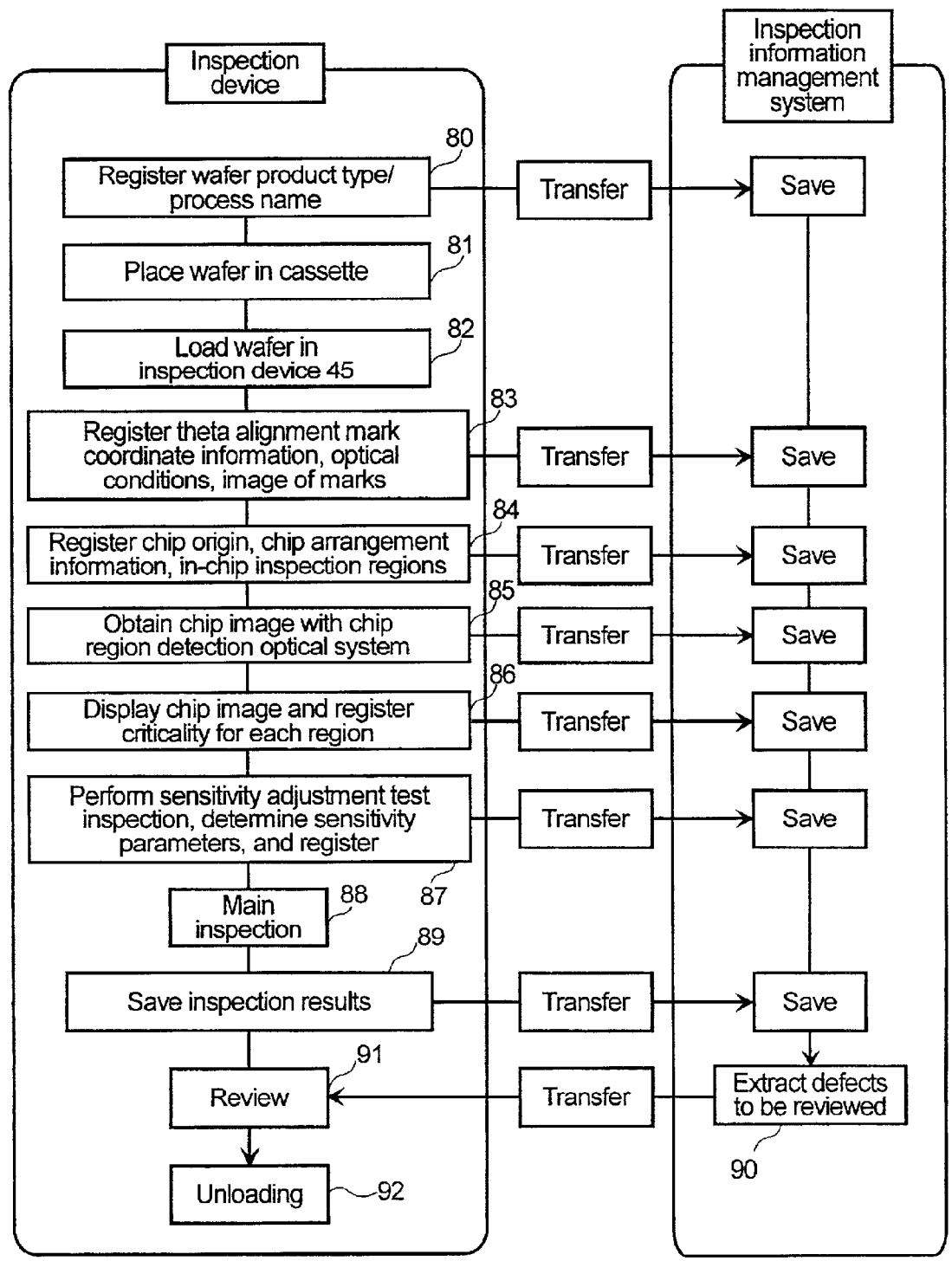
FIG. 11 is a flowchart showing the operation flow for inspecting a semiconductor wafer involving a new product type or process.

Using FIG. 11, the workflow involved in inspecting a wafer 1 involving a new product type or process.

FIG. 11 is a flowchart showing the sequence of operations performed when a wafer involving a new product type or new process is inspected. To facilitate the description, the flow of operations performed by the inspection device will be presented first.

At step 80, the inspection device first registers the product type and process into the first inspection device, e.g., the optical visual inspection device 45. Next, at step 81, the wafer 1 is placed in the cassette 41, and the wafer is loaded into the first inspection device at step 82.

Next, at step 83, information about the coordinates of the θ alignment marks of the wafer 1 is registered, and the optical conditions for retrieving images of the alignment marks are set up. Also, images of the alignment marks are retrieved and registered as template images.

Next, at step 84, chip origins, chip arrangement information, and in-chip inspection regions are registered. Next, at step 85, the chip detection optical system 20 retrieves an image of an entire chip. At step 86, the retrieved chip image is shown on the display of the operating computer 35, and this displayed image is used to define and register regions according to criticality.

Next, at step 87, differential images with adjacent chips are determined and a test inspection is performed to determine detection sensitivity parameters such as concentration threshold values used to evaluate defects. These detection sensitivity parameters are registered.

An inspection recipe is generated based on the information registered at step 80, step 83, step 84, step 85, step 86, and step 87. The registered information is all transferred to and saved at the inspection information management system 49 as well.

At step 88, the main inspection is performed using the inspection recipe generated previously. At step 89, the inspection results are saved and also transferred to the inspection information management system 49, where they are saved.

In the main inspection at step 88, the inspection recipe generated previously is used to determine differential images between adjacent chips or differential images between identically shaped patterns within a single chip, and the inspection sensitivity parameters set up at step 87 are used to detect defects.

In the inspection information management system 49, the defects to be reviewed are extracted at step 90, and the extraction results are transferred to the first inspection device 45 or another inspection device, e.g., an SEM review device or the like.

At step 91, the first inspection device 45 reviews defects based on the transferred extraction results. After the reviewing operation, the wafer 1 is unloaded and stored in the wafer cassette 41 at step 92 (see FIG. 1).

If a wafer 1 of the identical product type or process is to be inspected later by a different inspection device of the same device type, the inspection recipe stored in the inspection information management system 49 is transferred to the inspection device and inspection is performed. Furthermore, if an inspection is to be performed by an inspection device of a different device type, information registered in the inspection information management system 49 that can be shared is used to reduce the time required to generate recipes.

Also, by transferring inspection results to the inspection information management system 49 and extracting defects to be reviewed based on criticality, killer defects can be discovered at an early stage, and measures can be taken quickly in response to reduced product yield.

Preparing inspection recipes ahead of time is useful for performing inspections efficiently using inspection devices of different types. These inspection recipes must include information about die arrangement within wafers, information about in-die inspection area coordinates, and detection sensitivities. Of these, die arrangement information and in-die inspection area coordinate information can be shared via the inspection information management system 49.

However, detection sensitivities must be adjusted according to the product type and process of the wafer 1. Standard parameters for determining detection sensitivity include defect evaluation threshold values, magnifications of the optical system performing inspection, and illumination conditions. Sensitivity adjustments become very time-consuming if inspection parameters are determined by performing test inspections while modifying each of these parameters and performing reviews each time.

A more efficient method is to prepare multiple recipes with different sensitivities ahead of time and to perform test inspections using each of these. Then, the inspection results can be combined into a single set of inspection results and a review can be performed based on this.

FIG. 12 shows an example of this. FIG. 12(a) and FIG. 12(b) show results of inspections using two types of recipes. FIG. 12(c) shows the results of combining the results from these two types of recipes. The inspection results 1 and the inspection results 2 shown in FIG. 12(a) and FIG. 12(b) contain coordinates of defects. The coordinate information from the inspection results are compared, and defects at the same coordinates are combined and stored in the composite inspection results in FIG. 12(c).

For example, defect number 1 from FIG. 12(a) and defect number 1 from FIG. 12(b) are at roughly identical positions within the same die. A comparison of the in-die coordinates (X, Y) indicates that there is an offset of approximately 3 microns. This offset is affected by the margin of error in the defect coordinates precision of the inspection device.

Thus, when comparing coordinates from the inspection results in FIG. 12(a) and FIG. 12(b), a position offset tolerance must be set up according to the defect coordinate precision of the inspection device. This must be set according to the defect coordinate precision of the inspection device.

The composite inspection results in FIG. 12(c) must indicate if defects were found in the inspection results from both FIG. 12(a) and FIG. 12(b). Thus, for the inspection results 1 and the inspection results 2, FIG. 12(c) stores a "1" if a defect was detected and a "0" if a defect was not detected.

Figure 13:
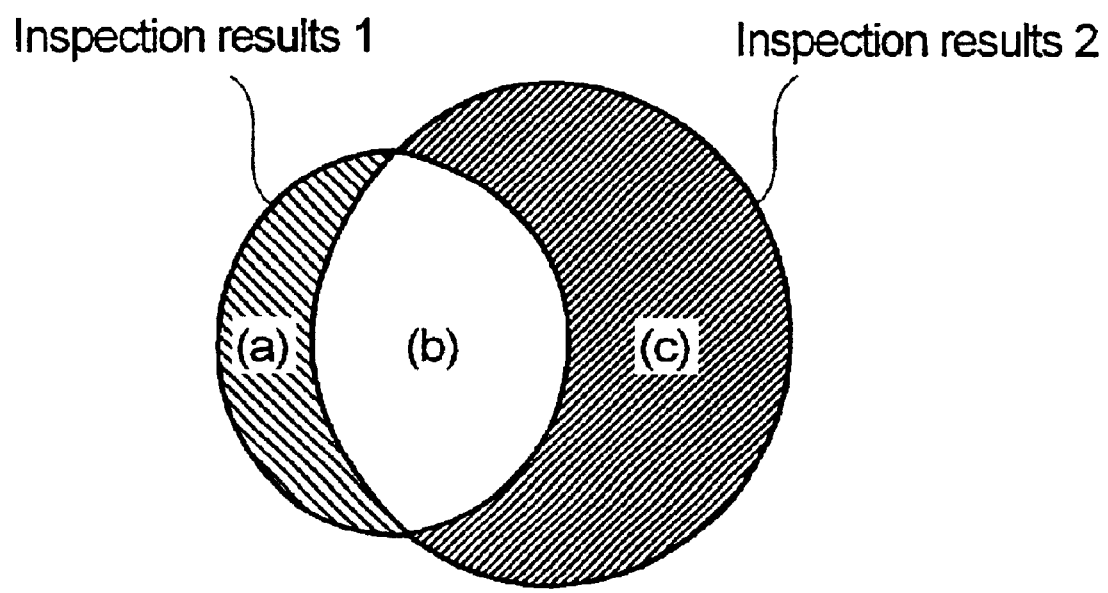
FIG. 13 is a Venn diagram of multiple inspection results.

FIG. 13 shows a schematic diagram showing a Venn diagram of the composite inspection results. For example, when performing a review to determine inspection sensitivity conditions, it would be more efficient to only review the defects from (a) and (c) from only one of the inspection results and to select appropriate sensitivity conditions for the main inspection based on this. The region (b) of FIG. 13 represents defects which are common to the inspection results 1 and 2.

This embodiment presents two-inspection conditions but similar operations can be performed for more inspections. Also, if different types of inspection devices are used, the inspection results from these inspection devices can be combined into one set of inspection results before performing a review. This can be used to determine which device type provides the inspection with the highest sensitivity, thus simplifying the selection of the inspection device to be used.

What is described here is one embodiment of the present invention, but other combinations of what is described can be implemented. Also, optical visual inspection devices and laser-scattering optical contaminant inspection devices can be expected to provide shorter and shorter wavelengths in order to improve inspection sensitivity. An example of this is inspection devices that use DUV (Deep Ultra-Violet) light. The present invention can also be used for inspection devices that will be developed in the future such as optical visual inspection devices and laser-scattering optical contaminant inspection devices that use short-wavelength lights.

With the present invention as described above, an image of a chip formed on a specimen is divided into inspection regions based on criticality, thus providing high-sensitivity inspection in these regions without false detections. Also, since the system allows sharing of inspection conditions that can be used by multiple inspection devices, conditions can be determined more quickly.

Furthermore, by performing post-processing by defined in-chip regions to eliminate false detections, reviews and automatic defect classification can be made more efficient. This allows early discovery of killer defects and quicker counter-measures, leading to improved product yield.

Furthermore, stability in and differences between inspection devices can be monitored, and different types of inspection devices can be used in an optimal manner, thus providing stable operations of the inspection system. This allows stable high-yield production from the production line.

As described above, the present invention provides high-sensitivity inspection without false detections in partitioned regions. Also, inspection conditions that are common to different inspection devices can be shared, allowing conditions to be determined more quickly. Furthermore, post-processing for the removal of false detections in in-chip regions can be performed to improve the efficiency of review and automatic defect classification operations.

The invention may be embodied in other specific forms without departing from the spirit or essential characteristics thereof. The present embodiment is therefor to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A method for inspecting defects on a specimen comprising the following steps:

imaging a specimen processed by a predetermined process and obtaining an image of said specimen by a first image detector with a magnification;

dividing said obtained image into plural regions and setting up defect detection sensitivities for individual regions so that regions located at peripheral portions of said image of said specimen have a lower sensitivity than a sensitivity of regions located at central portions of said image of said specimen based on information from said image;

obtaining an image of said specimen by a second image detector with a magnification; and detecting defects on said specimen by processing said image obtained by said second image detector based on said defect detection sensitivities set up for said individual regions.

2. A method for inspecting defects on a specimen as described in claim 1 wherein:

said specimen is a semiconductor wafer containing a plurality of chips, an identical pattern being formed on each of said plurality of chips; and said defect detection sensitivities for said individual regions are provided for each of said plurality of chips formed on said semiconductor wafer.

3. A method for inspecting defects on a specimen as described in claim 1 wherein:

said specimen is a semiconductor wafer containing a plurality of chips, an identical pattern being formed on each of said plurality of chips; and said defect detection sensitivities for said individual regions are provided for regions within said plurality of chips formed on said semiconductor wafer.

4. A method for inspecting defects on a specimen as described in claim 1 wherein:

said specimen is a semiconductor wafer containing a plurality of chips, an identical pattern being formed on each of said plurality of chips; and said defeat detection sensitivities for said individual regions are determined using information about differences between image data from adjacent ones of said plurality of chips.

5. A method for inspecting defects on a specimen as described in claim 1 wherein said defect detection sensitivities for said individual regions are provided according to the probability of killer defects being generated in said individual regions.

6. A method for inspecting defects on a specimen as described in claim 1 wherein:

selected defects to be re-examined are selected from said detected defects; and said selected defects are imaged again and images of said selected defects are obtained again.

7. A method for inspecting defects on a specimen as described in claim 6 wherein said defect detection sensitivities are changed based on said images of said selected defects which are obtained again.

8. A method for inspecting defects on specimens comprising the following steps:

imaging a specimen processed by a predetermined process and obtaining an image of said specimen by a first image detector with a magnification, a plurality of identical sets of patterns being formed on said specimen;

dividing said obtained image into plural regions and setting up defect detection sensitivities for individual regions so that regions located at peripheral portions of said image of said specimen have a lower sensitivity than a sensitivity of regions located at central portions of said image of said specimen based on information from said image;

obtaining an image of said specimen by a second image detector with a magnification;

detecting defects on said specimen by processing said image obtained by second image detector based on said defect detection sensitivities for individual regions;

storing said detected defects;

selecting defects to be re-observed out of said stored defects; and observing said selected defects.

9. A method for inspecting defects on specimens as described in claim 8 wherein:

said specimen is a semiconductor wafer containing a plurality of chips, said identical sets of patterns being formed on each of said plurality of chips; and said defect detection sensitivities for individual regions are provided for each of said plurality of chips formed on said semiconductor wafer.

10. A method for inspecting defects on specimens as described in claim 8 wherein said defect detection sensitivities are changed based on results of observing said selected defects.

11. A method for inspecting defects on specimens comprising the following steps:

selling up a first defect detection condition and a second defect detection condition;

imaging a specimen processed by a predetermined process and obtaining an image of said specimen;

detecting defects on said specimen by processing said image using said first defect detection condition;

storing information of defects detected by using said first defect detection condition;

detecting defects on said specimen by processing said image using a second defect detection condition;

storing information of defects detected by using said second defect detection condition;

selecting either said first defect detection condition or said second defect condition based on said stored information of defects;

setting up a selected defect detection condition selected at the step of selecting; and detecting defects on another specimen by using said selected defect detection condition set up at the setting up step.

12. A method for inspecting defects on specimens as described in claim 11 wherein said detection of defects on said another specimen involves excluding defects appearing in both said stored information about defects detected using said first defect detection condition and said stored information about defects detected using said second defect detection condition.

* * * * *